United States Patent [19]

Sato et al.

[11] Patent Number: 5,132,454
[45] Date of Patent: Jul. 21, 1992

[54] OXAMIC ACID COMPOUNDS AND PHARMACEUTICAL COMPOSITIONS FOR USE IN IMPROVEMENT OF DAMAGED CEREBRAL FUNCTIONS OF BRAIN

[75] Inventors: Yasuo Sato, Yokohama; Shinsuke Kato, Sendai; Takako Taniguchi, Yokohama; Kunio Atsumi, Yokohama; Mitsugu Hachisu, Yokohama; Seiji Shibahara, Yokohama, all of Japan

[73] Assignee: Meiji Seika Kaisha, Ltd., Japan

[21] Appl. No.: 662,192

[22] Filed: Feb. 28, 1991

Related U.S. Application Data

[63] Continuation of Ser. No. 489,358, Mar. 6, 1990, Pat. No. 5,066,077.

[30] Foreign Application Priority Data

Mar. 8, 1989 [JP] Japan ................................. 1-53687

[51] Int. Cl.⁵ ........................................ C07C 229/26
[52] U.S. Cl. ..................................... 562/561; 514/563
[58] Field of Search ......................... 562/561; 514/563

[56] References Cited

U.S. PATENT DOCUMENTS

| 3,658,994 | 4/1972 | Kaiser et al. | 562/561 |
| 4,216,238 | 8/1980 | Baker et al. | 562/561 |
| 4,299,979 | 11/1981 | Murphy | 562/561 |

*Primary Examiner*—James H. Reamer
*Attorney, Agent, or Firm*—Lalos & Keegan

[57] ABSTRACT

A method of inhibiting the abnormal postnatal axial growth of the eye of a maturing animal during conditions ordinarily leading to said abnormal growth, which comprises (1) determining the neurochemical present in the retina of said eye, e.g., dopamine, the concentration of which is reduced during said conditions, and (2) administering to said eye during postnatal maturation effective amounts of said neurochemical, its agonist or its antagonist.

3 Claims, No Drawings

OXAMIC ACID COMPOUNDS AND PHARMACEUTICAL COMPOSITIONS FOR USE IN IMPROVEMENT OF DAMAGED CEREBRAL FUNCTIONS OF BRAIN

This is a continuation of copending application Ser. No. 07/489,358 filed on Mar. 6, 1990, now U.S. Pat. No. 5,066,677.

SUMMARY OF THE INVENTION

This invention relates to novel and useful oxamic acid compounds, particularly novel N-(dialkylaminoalkyl)-substituted derivatives or N-(dialkylaminoalkyl)-N-alkyl substituted derivatives of oxamic acid, which exhibit cerebral protective effect against cerebral anoxia (a reduced oxygen-supply from the blood) as induced in the brain of a mammalian animal, including human, by subjecting the animal to hypoxic conditions, and which owing to their cerebral protective effect, have medicinal effects of improving or ameliorating different symptoms of cerebral disorders or diseases caused by damaged or disturbed intracerebral energy metabolism. This invention also relates to a new pharmaceutical composition comprising said novel oxamic acid compound as the active ingredient. This new pharmaceutical composition is particularly of utility as a drug for improving or ameliorating the damaged or disturbed cerebral functions of the brain of a mammalian animal, including human. This invention also include new medicinal use of said novel N-substituted or N,N-di-substituted oxamic acid compounds. Furthermore, this invention relates to a process for the preparation of these novel and useful oxamic acid compounds.

BACKGROUND OF THE INVENTION

Reflecting the advent of the so-called "high-age" society, it has become a serious public concern to develop medical measures for treatment of senile dementia as caused by damages or disturbances of the cerebral functions which are, in turn, attributable to cerebrovascular diseases or damages or disturbances of intracerebral energy metabolism. A variety of drugs have heretofore been developed as anti-dementia drugs. At the present status, senile dementia, and amnesia as caused by cerebrovascular diseases as well as the biological mechanisms of occurrence of these disorders or diseases have not yet been elucidated fully. In these circumstances, no sufficient clue has yet been established to discover and screen effective cerebral drugs. As experimental methods for inducing amnesia in normal mammalian animals, it is known to administer such an agent which inhibits the in vivo synthesis of nucleic acids or proteins, or an anticholinergic agent. Amnesia is also known to be inducible by cerebral anoxia, ischemic load or the like. With using such model animals which have amnesia induced by these causative agents, it has been attempted to detect and develop cerebral drugs which are capable of amelioratively treating or preventing the amnesia. In addition, with using such model animals which have cerebral anoxia induced either by giving a lethal dose of potassium cyanide or by subjecting to hypobaric or normobaric hypoxic conditions, namely, the reduced oxygen-supply conditions, attempts have also been made to develop cerebral drugs which are effective for the improvement or amelioration of cerebral circulation metabolism or intracerebral energy metabolism. These matters are referred to e.g. in "Folia Pharmacol. Japan", 85, 323–328 (1985); ibid., 86, 445–456 (1986): and Japanese Patent Application first publication "Kokai" No. 117468/79 or its corresponding U.S. Pat. No. 4,369,139.

It is well accepted that oxygen deprivation is one of the most damaging conditions affecting the animal or human brain, and that when oxygen supply to the brain becomes deficient, cerebral functions cease after brief periods of cerebral anoxia and tissue destruction ensues. Consequently, any suitable agents which enable the brain to withstand even mild degree of cerebral anoxia would be expected to be useful as a cerebral protective agent or a drug for improving or ameliorating the damaged or disturbed cerebral functions of brain (the drug of this utility is hereinafter sometimes merely called as "a cerebral drug"). Many compounds have been investigated for their cerebral protective effect on cerebral anoxia which is experimentally induced by subjecting the animal to hypoxic conditions, whereby there is obtained a suggestion or indication that the tested compounds are effective for treatment of cerebral anoxic or ischemic diseases or disorders (see, e.g. "Arch. int. Pharmacodyn." 233, 136–144 (1978) and "Life Science" 13, 467–474 (1973)).

However, the cerebral drugs which have been provided so far can hardly be said to have fully satisfactory effects and proven reliability. Under these circumstances, there remains a demand for the development of new cerebral drugs which are still stronger and safer than the known drugs as provided to date.

An object of this invention is to prepare and provide novel compounds having excellent pharmacological effects for the improvement of the damaged or disturbed cerebral functions of the brain as well as a high level of safety with being free of side effects. Another object of this invention is to provide novel cerebral drugs. To achieve these objects, we, the present inventors, and our associates have proceeded with extensive investigations. As a result, we have found that compounds having anti-anoxia effects, in other words, cerebral protective effect against cerebral anoxia are useful or promising as drugs having medicinal effects capable of treating cerebration disorders of mammals, including human, when such compounds are effective in significantly prolonging the survival time of mice having cerebral anoxia experimentally induced under hypobaric hypoxia conditions in the experiments wherein the cerebral anoxia mice are used as model animals. We and our associates already tested the cerebral protective effect against cerebral anoxia of some known N,N-dialkyloxamic acids (which may also be called N,N-dialkyloxaminic acids) which are disclosed in Japanese Patent Application first publication "Kokai" No. 24823/79. Moreover, we also synthetized another N,N-di-substituted oxamic acid compounds and assayed the cerebral protective effect of these another compounds against cerebral anoxia.

As a result of our above-mentioned earlier investigations and tests, we already found that N,N-di-alkyl-substituted or N,N-di-alkenyl-substituted oxamic acid compounds which may generally be represented by the following formula (A):

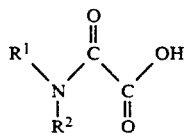

wherein $R^1$ and $R^2$ may be the same or different and are individually a linear or branched alkyl group of 1 to 4 carbon atoms or an alkenyl group of 2 to 4 carbon atoms, or a pharmacologically acceptable salt thereof have the cerebral protective effect against cerebral anoxia and low toxicity, as well as their potential usefulness as the cerebral drugs (see Japanese patent application No. 164,938/88 or its corresponding European patent application No. 89306780.1 and its published specification No. 0350260A2 published Jan. 10, 1990 or its corresponding U.S. patent application Ser. No.373,469 filed on Jun. 30, 1989, pending).

In addition to our previous investigation about the N,N-di-alkyl-substituted or N,N-di-alkenyl-substituted derivatives of oxamic acid as represented by the above general formula (A), we, the present inventors, have now developed our investigations in an attempt to synthetize further novel N-mono-substituted or N,N-di-substituted derivatives of oxamic acid, and we have now succeeded in synthetizing as the new componds an N-(dialkylaminoalkyl)-substituted or N-(dialkylaminoalkyl)-N-alkyl-substituted oxamic acid compound having a general formula (I) described below. Furthermore, we have assayed this new N-mono-substituted or N,N-di-substituted oxamic acid compound of the formula (I) as synthetized, for its cerebral protective effect against cerebral anoxia.

As an outcome of our recent investigations and tests as above, we have now discovered that the new N-(dialkylaminoalkyl)-substituted or N-(dialkylaminoalkyl)-N-alkyl-substituted oxamic acid compound having the general formula (I) as described below exhibits the cerebral protective effect against cerebral anoxia and low toxicity, similarly to the N,N-dialkyl-substituted or N,N-di-alkenyl-substituted oxamic acid compound of the above formula (A) which is disclosed in the aforesaid Japanese patent application No. 164,938/88 or its corresponding European patent application published specification No. 0350260A2 or its corresponding U.S. patent application Ser. No. 373,469, pending, and that the new compound of the general formula (I) and a pharmaceutically acceptable salt thereof are expectable as being useful for the cerebral drugs.

In addition, we have also succeeded in providing a process which can advantageously produce the novel compounds of the formula (I) on a commercial scale.

DETAILED DESCRIPTION OF THE INVENTION

In a first aspect of this invention, therefore, there is provided as the new compounds an oxamic acid compound having the general formula:

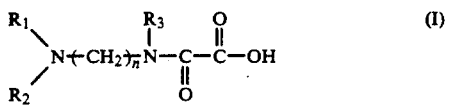

wherein $R_1$ and $R_2$ are same or different from each other and are individually a linear or branched alkyl group of 1 to 4 carbon atoms and $R_3$ is a hydrogen atom or a linear or branched alkyl group of 1 to 4 carbon atoms and n is an integer of 2 to 4, or a pharmacologically acceptable salt thereof.

In a second aspect of this invention, there is provided a pharmaceutical composition for use in improvement or amelioration of the damaged cerebral functions of brain of a mammalian animal, which comprises an oxamic acid compound having the formula (I) or a pharmacologically acceptable salt thereof, as active ingredient, in association with a pharmaceutically acceptable solid or liquid carrier for the active ingredient.

In particular, the pharmaceutical composition of the second aspect of this invention may be used as a cerebral protective agent, especially for protection against anoxic brain damages in a mammalian animal or for improvement or amelioration of the damaged cerebral functions of brain in a mammalian animal as induced due to low oxygen supply.

In a third aspect of this invention, there is provided a method for protecting against anoxic brain damages in a mammalian animal, which comprises parenterally or orally administering a pharmacologically effective amount of an oxamic acid compound having the formula (I) or a pharmacologically acceptable salt thereof, to the animal.

In a further aspect of this invention, there is provided a method for improving or ameliorating the damaged cerebral functions of brain in a mammalian animal as induced due to low oxygen supply, which comprises parenterally or orally administering a pharmacologically effective amount of an oxamic acid compound having the formula (I) as defined in the above or a pharmacologically acceptable salt thereof, to the animal.

When the compound of the formula (I) is administered to the animal or human to be treated, it may be given parenterally, for example, intramuscularly, intravenously, intraperitoneally, subcutaneously, rectally, or orally.

This invention further includes use of the new oxamic acid compound having the formula (I) defined in the above or a pharmacologically acceptable salt thereof, as a cerebral protective agent, especially as an agent for protecting against anoxic brain damages in a mammalian animal, or as an agent for improving or ameliorating the damaged cerebral functions of brain of a mammalian animal as induced by disturbance of the cerebral energy metabolism.

For the N-mono-substituted or N,N-di-substituted derivatives of oxamic acid having the general formula (I) according to this invention, specific examples of the linear or branched alkyl group of 1-4 carbon atoms which are represented by $R_1$, $R_2$ and $R_3$ in the formula (I), include methyl, ethyl, n-propyl, isopropyl, n-butyl, isobutyl, sec-butyl, tert-butyl, and the like.

Suitable examples of the new compound of the formula (I) according to the first aspect of this invention include N-dimethylaminoethyloxamic acid; N-dimethylaminopropyloxamic acid; N-diethylaminoethyloxamic acid; and N-diethylaminopropyloxamic acid; as well as N-dimethylaminoethyl-N-methyloxamic acid; N-dimethylaminopropyl-N-methyloxamic acid; N-diethylaminoethyl-N-methyloxamic acid; and N-diethylaminopropyl-N-methyloxamic acid, and their sodium salts, potassium salts and hydrochlorides.

Illustrative examples of the pharmacologically acceptable salt of the compound having the formula (I) according to this invention include a salt of the carboxyl group of the compound with a pharmaceutically acceptable metal, especially, conventional non-toxic salts, for example, alkali metal salts such as the sodium salt and potassium salt, alkaline earth metal salts such as the calcium salt and magnesium salt, and the ammonium salt. Also mentioned are various addition salts of the compound (I) with organic basis, for examples, salts with lower alkylamines such as triethylamine, addition salts with organic amines such as the pyridine, ethanolamine, triethanolamine and dicyclohexylamine salts, and addition salts with basic amino acids such as arginine. Addition salts of the compound (I) may further include such acid-addition salts of the compound (I) with a non-toxic acid such as hydrochloric, sulfuric, nitric, phosphoric acids, and acetic, propionic, maleic acids and the like.

The novel compounds of the formula (I) according to this invention can each be prepared by such a process which comprises hydrolyzing an oxamic acid ester compound having the formula (II) shown below, according to the following reaction equation:

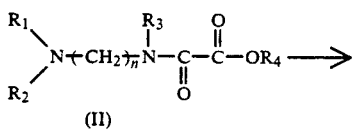

(II)

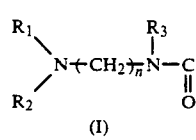

(I)

wherein $R_1$, $R_2$, $R_3$ and n have the same meanings as defined above, and $R_4$ denotes a linear or branched alkyl group having 1-4 carbon atoms, an aralkyl group such as benzyl or an aryl group such as phenyl.

In another aspect of this invention, therefore, there is provided a process for the preparation of the oxamic acid compound having the formula (I) defined in the above, which comprises hydrolyzing an oxamic acid ester compound having the following formula

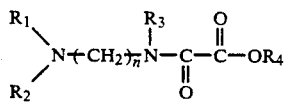  (II)

wherein $R_1$ and $R_2$ are same or different from each other and are individually a linear or branched alkyl group of 1 to 4 carbon atoms, $R_3$ is a hydrogen atom or a linear or branched alkyl group of 1 to 4 carbon atoms, and n is an integer of 2 to 4, and $R_4$ denotes a linear or branched alkyl group of 1 to 4 carbon atoms, an aralkyl group or an aryl group.

Specific examples of the linear or branched alkyl group of 1-4 carbon atoms, which is represented by $R_1$, $R_2$ and $R_3$ in the starting ester compound of the general formula (II), include methyl, ethyl, n-propyl, isopropyl, n-butyl, isobutyl, sec-butyl and tert-butyl. Specific examples of the linear or branched alkyl group of 1-4 carbon atoms which is represented by $R_4$ include methyl, ethyl, n-propyl, isopropyl, n-butyl, isobutyl, sec-butyl, tert-butyl, and the line. On the other hand, illustrative examples of the aralkyl group as represented by $R_4$ include a phenyl-$(C_1-C_4)$-alkyl groups such as benzyl and phenethyl. Further, exemplary aryl groups represented by $R_4$ include unsubstituted or substituted phenyl groups.

The hydrolytic reaction of the starting ester compound of the formula (II) may be conducted at $-10°$ C. to $50°$ C., for a time of 0.1 hours to several hours, in the presence of a base, in water or an aqueous organic solvent. Examples of the organic solvent include alcohols such as methanol, ethanol and propanol; and aprotic solvents such as 1,4-dioxane, tetrahydrofuran and pyridine. Examples of the available base include alkali metal hydroxides such as sodium hydroxide and potassium hydroxide; alkaline earth metal hydroxides such as magnesium hydroxide and calcium hydroxide; quaternary ammonium hydroxides such as tetrabutylammonium hydroxide and benzyltrimethyl ammonium hydroxide; alkali metal carbonates such as sodium carbonate and potassium carbonate; tertiary amines such as trialkylamines, e.g., triethylamine, N-methylpiperidine and 4-(N,N-dimethylamino)pyridine; etc.

The starting ester compound having the formula (II) can be prepared, for example, by such a method in which an amine compound of the formula (III) is condensed with a (chloroformyl)formic acid ester of the formula (IV) shown below, according to the following reaction equation:

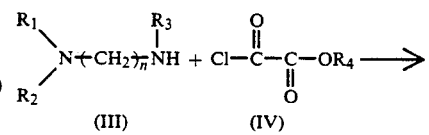

(III)              (IV)

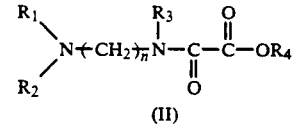

(II)

wherein $R_1$, $R_2$, $R_3$, $R_4$ and n have the same meanings as defined above.

The toxicity of the compounds of the general formula (I) usable in this invention was evaluated by using N-dimethylaminoethyl-N-methyloxamic acid as one example. When 3 ddY-mice (male, 5 weeks-old, body weight: 25 g) in each group were administered intravenously with a dose of 1000 mg/kg of the test compound, all the mice tolerated it and remained alive, thereby demonstrating that the compounds usable in this invention have low toxicity and are useful as cerebral protective agent or as agent for therapeutically treating and improving the damaged cerebral functions of mammalian animal brain.

The pharmaceutical composition according to this invention which comprises one or more of the compounds of the general formula (I) and a salt thereof as the active ingredient may be formulated into various preparation forms, primarily, as injections such as intravenous injections, oral preparations such as capsules, tablets and powders, rectal preparations, fat-and-oil base suppositories, water-soluble suppositries, etc. These various preparations can be produced in a manner known per se in the art, using one or more of excipients, extenders, binders, wetting agents, disintegrators, surfactants, lubricants, dispersants, buffers, preservatives, solubilizers, antiseptics, corrigents, soothing agents and the like. Specific illustrative methods of preparing some medicinal preparations will be described in Examples 6-8 given hereinafter.

The dose of each compound of the formula (I) can be suitably determined for each case by taking into consideration the symptom, age, sex, etc. of patients to be treated. For a general guideline, the daily dose of the compound may range from 250 mg to 3000 mg per adult. This dose may usually be administered in 1-4 portions a day.

The pharmacological effect of the compounds of general formula (I) according to this invention is now illustrated in the following test:

Test 1

The cerebral protective effect or the improving or ameliorative effect on the damaged cerebral functions of the oxamic acid compounds of the formula (I) of this invention was examined in terms of their effect that can prolong the survival time of such mice having cerebral anoxia experimentally induced under the conditions of loading the hypobaric hypoxia.

Male, ddY mice (6 weeks old, body weight: 25-30 g, each group comprising 6 mice) were administered intraperitoneally with the compounds of this invention, respectively, which were synthetized in the Examples 3-5 of this invention as given hereinafter. Each of the tested compounds of this invention had been beforehand dissolved in redistilled water and the resulting test aqueous solution was intraperitoneally administered to the mice in an amount of 0.1 ml of the solution per 10 g body weight. Thirty minutes after the intraperitoneal administration of the test solution, the mice were individually placed in hermetic transparent containers. The containers were rapidly evacuated to 190 mmHg by means of a vacuum pump. Time was measured from the initiation of the evacuation to the death of each mouse due to respiratory failure. That time was recorded as the survival time (seconds) of mice.

The ratios of the survival time of the groups of the treated mice which received the administration of the tested compounds of this invention, as divided by the survival time of a control group of mice (untreated) which received no administration of the drug were calculated. The ratios are shown in Table 1 below.

they have the effects of promoting the supply of oxygen from blood to the brain, reducing the wasteful consumption of oxygen and ATP in the brain and enhancing the formation of ATP in the brain.

In clinical applications, the compounds of the formula (I) of this invention and their salts are believed to be effective especially for the improvement of hypobulia, emotional troubles and the like, which tend to occur as sequela of cerebral infarction, intracerebral bleeding, etc. The compounds of this invention and their salt are also believed to be effective as therapeutic agents for senile dementia in view of their effectiveness for the improvement of hypobulia.

This invention is now illustrated by the following Examples. Thus, Examples 1 and 2 show the preparation of certain starting esters of formula (II) and Examples 3 to 5 show the preparation of typical compounds of formula (I) according to this invention.

EXAMPLE 1

Synthesis of methyl N-dimethylaminoethyl-N-methyloxamate hydrochloride

N-Dimethylaminoethyl-N-methylamine (500 mg) was dissolved in water (20 ml) and the solution was cooled to −78° C. on a dry ice/acetone bath under stirring, and methyl (chloroformyl) formate (599 mg) was then added dropwise thereto. The reaction mixture was stirred for further 2 hours while gradually raising the temperature of the reaction vessel up to room temperature. The resulting precipitate was recovered by filtration and washed with methylene chloride and then with n-hexane, affording methyl N-dimethylaminoethyl-N-methyloxamate hydrochloride (755 mg) in the form of a white solid.

$^1$H-NMR, $\delta$(D$_2$O): 4.06(3H, s), 4.01–3.88(2H, m), 3.65–3.54(2H, m), 3.09(6H, s)

EXAMPLE 2

Synthesis of methyl N-dimethylaminoethyloxamate hydrochloride

TABLE 1

| Name of test compound | Structure of test compound | Dose of test compound (mg/kg) | Survival time ratio |
|---|---|---|---|
| Control (untreated) | — | — | 100 |
| N-dimethylamino-ethyloxamic acid hydrochloride (the product of Example 4) | [(H$_3$C)$_2$—N—CH$_2$CH$_2$—NH—CO—COOH]HCl | 100 | 148 |
| N-dimethylamino-ethyl-N-methyl-oxamic acid hydrochloride (the product of Example 3) | [(H$_3$C)$_2$—N—CH$_2$CH$_2$—N(CH$_3$)—CO—COOH]HCl | 100 | 204 |

As is apparent from the foregoing tests, the compounds of the formula (I) of this invention can achieve a significant prolongation of the survival time of animals having the cerebral anoxia induced by conditions of hypobaric hypoxia and thus can exhibit the protective effects against cerebral anoxia.

It is believed that the compounds of the formula (1) according to this invention have the activities of improving or ameliorating the cerebral energy mechanism and circulation in a mammalian animal owing to that Starting from N-dimethylaminoethylamine, the titled compound was obtained in the same manner as in Example 1.

$^1$H-NMR, $\delta$(D$_2$O): 3.78(3H, s), 3.72–3.45(4H, m), 2.82(6H, s)

EXAMPLE 3

Preparation of N-dimethylaminoethyl-N-methyloxamic acid hydrochloride

Methyl N-dimethylaminoethyl-N-methyloxamate hydrochloride (500 mg) was dissolved in water (20 ml) and the resulting solution was cooled on an ice bath under stirring. To this cooled solution was added dropwise a solution of sodium hydroxide (356 mg) in water (10 ml). After the completion of the addition, the ice bath was removed and the reaction solution was stirred at room temperature for further 1 hour and then adjusted the pH thereof to 4 with the addition of 1N aqueous HCl. The solvent was distilled off under a reduced pressure and the residue was dissolved in a small amount of water and subjected to chromatographic separation and purification on a resin,"Diaion IRA-400" ion-exchange resin using water 1N aqueous NCl as eluent. The eluates are distilled under a reduced pressure to remove the solvent, yielding N-dimethylaminoethyl-N-methyloxamic acid hydrochloride (395 mg) as a white power $^1$H-NMR, $\delta(D_2O)$: 4.05–3.70(2H, m), 3.65–3.30(2H, m) 3.20–2.85(9H, m)

IR absorption (cm$^{-1}$, Nujol): 1756, 1645, 1347, 1262, 1240

EXAMPLE 4

Preparation of N-diemthylaminoethyloxamic acid hydrochloride

The titled compound was synthesized in the same manner as in Example 3 except that methyl N-dimethylaminoethyloxamate hydrochloride was used as starting compound.

$^1$H-NMR, $\delta(D_2O)$: 3.75–3.65(2H, broad t), 3.43–3.35(2H, broad t), 2.95(6H, s)

IR absorption (cm$^{-1}$, Nujol):
1748, 1705, 1678, 1536, 1361, 1270

EXAMPLE 5

Preparation of N-dimethylaminoethyl-N-methyloxamic acid

A solution of methyl N-dimethylaminoethyl-N-methyloxamate hydrochloride (500 mg) in water (20 ml) was cooled on an ice bath under stirring, and to the solution was added dropwise a solution of sodium hydroxide (356 mg) in water (10 ml). After the completion of the addition, the reaction solution was further stirred at room temperature for 2 hours and then adjusted the pH thereof to 4 with the addition of 1N aqueous HCl. After the removal of the solvent by distillation under a reduced pressure, methanol (20 ml) was added to the distillation residue and solid matters which remain undissolved were removed by filtration. The filtrate was concentrated and then purified by chromatography on a resin "Sephadex LH-20" using a 1:1 (by volume) mixture of methylene chloride-methanol as eluent, affording N-dimethylaminoethyl-N-methyloxamic acid (250 mg) as a white solid.

$^1$H-NMR, $\delta(D_2O)$: 3.80–3.40(2H, m), 3.11, 3.02(3H, s×2), 2.90–2.50(2H, m), 2.37, 2.35(6H, s×2)

IR absorption (cm$^{-1}$, Nujol): 1621, 1501, 1433, 1363, 1242

Some methods of preparing typical formulations will be illustrated in Examples 6–8 given hereinafter which by no means limit this invention.

EXAMPLE 6

One part of N-dimethylaminoethyl-N-methyloxamic acid, 2.7 parts of lactose, 0.8 parts of corn starch and 0.05 parts of polyvinylpyrolidone, all on weight basis, were mixed and the mixture was wetted with ethanol, granulated in a usual manner, dried, screened and then mixed with 0.5% of magnesium stearate. The resulting mixture was compressed and formed into 100 mg-tablets in an usual manner.

EXAMPLE 7

Five grams of N-dimethylaminoethyl-N-methyloxamic acid and 5 g of mannitol were dissolved in distilled water to give a total volume of 1000 ml. After sterilizing the aqueous solution in a usual manner, it was filled in 2 ml-portions into vials and then lyophilized. Upon use, the lyophilized preparation is dissolved in sterile distilled water to prepare an injectable solution.

EXAMPLE 8

One part of N-diemthylaminoethyl-N-methyloxamic acid and 4 parts of lactose, all on weight basis, were well mixed together and the mixture was sifted through a 50 mesh sieve to prepare a power preparation.

We claim:

1. An oxamic acid compound for use in improvement or amelioration of the damaged cerebral functions of the brain of a mammalian animal having the general formula (I):

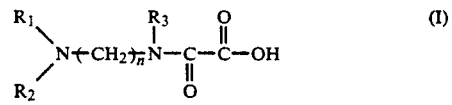

wherein $R_1$ and $R_2$ are same or different from each other and are individually linear or branched alkyl group of 1 to 4 carbon atoms and $R_3$ is a hydrogen atom or a linear or branched alkyl group of 1 to 4 carbon atoms and n is an integer of 2 to 4, or a pharmacologically acceptable salt thereof.

2. A pharmaceutical composition for use in improvement or amelioration of the damaged cerebral functions of the brain of a mammalian animal, which comprises an oxamic acid compound having the general formula (I):

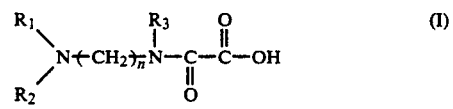

wherein $R_1$ and $R_2$ are same or different from each other and individually a linear or branched alkyl group of 1 to 4 carbon atoms and $R_3$ is a hydrogen atom or a linear or branched alkyl group of 1 to 4 carbon atoms and n is an integer of 2 to 4, or a pharmacologically acceptable salt thereof as an active ingredient, in association with a pharmaceutically acceptable solid or liquid carrier for the active ingredient.

3. The pharmaceutical composition of claim 2 which is used as a cerebral protective agent, especially for protection against anoxic brain damages in a mammalian animal or for improvement or amelioration of the damaged cerebral functions of the brain in a mammalian animal as induced due to low oxygen supply.

* * * * *

UNITED STATES PATENT AND TRADEMARK OFFICE
CERTIFICATE OF CORRECTION

PATENT NO. : 5,132,454

DATED : July 21, 1992

INVENTOR(S) : Yasuo Sato, et al

It is certified that error appears in the above-identified patent and that said Letters Patent is hereby corrected as shown below:

On the title page, delete the entire Abstract and substitute the following Abstract:

Novel N-(dialkylaminoalkyl)-substituted derivatives or N-(dialkylaminoalkyl)-N-alkyl-substituted derivatives of oxamic acid are now synthetized and found to exhibit the cerebral protective effect against cerebral anoxia in brain of a mammalian animal, including human, and to be useful as an agent for improving or ameliorating the damaged or disturbed functions of the brain.

Signed and Sealed this

Twentieth Day of April, 1993

*Attest:*

MICHAEL K. KIRK

*Attesting Officer*     *Acting Commissioner of Patents and Trademarks*